US 7,781,158 B2

(12) United States Patent
Yu et al.

(10) Patent No.: US 7,781,158 B2
(45) Date of Patent: Aug. 24, 2010

(54) METHOD OF SEPARATING COLLAGEN FROM THE VARIOUS ANIMAL TISSUES FOR PRODUCING COLLAGEN SOLUTION AND PRODUCT USING THE SAME

(75) Inventors: Ji-Chul Yu, Seoul (KR); Jae-Deog Jang, Seoul (KR); Cheong-Ho Chang, Seoul (KR); Sae-Bom Lee, Seoul (KR); Se-Geun Yeo, Gyeonggi-do (KR); Chang-Kwon Ko, Seoul (KR)

(73) Assignee: SEWON CELLONTECH Co., Ltd., Youngdeungpo-Gu, Seoul (KR)

( * ) Notice: Subject to any disclaimer, the term of this patent is extended or adjusted under 35 U.S.C. 154(b) by 93 days.

(21) Appl. No.: 11/885,386

(22) PCT Filed: Mar. 9, 2006

(86) PCT No.: PCT/KR2006/000849
§ 371 (c)(1),
(2), (4) Date: Aug. 30, 2007

(87) PCT Pub. No.: WO2006/096027
PCT Pub. Date: Sep. 14, 2006

(65) Prior Publication Data
US 2008/0118947 A1    May 22, 2008

(30) Foreign Application Priority Data
Mar. 11, 2005    (KR) .................... 10-2005-0020367

(51) Int. Cl.
*A01N 1/00* (2006.01)
*C12P 21/04* (2006.01)
*C12P 21/06* (2006.01)
*A61K 38/00* (2006.01)
*A61K 38/39* (2006.01)
*C07K 14/00* (2006.01)

(52) U.S. Cl. .................. 435/1.1; 435/68.1; 435/70.3; 514/12; 530/350; 530/356

(58) Field of Classification Search .................. None
See application file for complete search history.

(56) References Cited

U.S. PATENT DOCUMENTS

| 4,294,753 A | * | 10/1981 | Urist ........................... 530/395 |
| 4,434,094 A | * | 2/1984 | Seyedin et al. .............. 530/416 |
| 4,550,080 A | * | 10/1985 | Hasegawa et al. ........... 435/212 |
| 5,171,574 A | * | 12/1992 | Kuberasampath et al. ... 424/423 |
| 6,548,077 B1 | * | 4/2003 | Gunasekaran ............... 424/422 |

* cited by examiner

*Primary Examiner*—Christopher R Tate
*Assistant Examiner*—Aaron J Kosar
(74) *Attorney, Agent, or Firm*—GWiPS (57) ABSTRACT

A method for separation the collagen from the various animal tissues is disclosed for preparing collagen solution and product using the same. The porcine tissues are processed to have proper form and size for acid-treatment. The acid-treatment is repeated with pepsin to separate type I or II collagens. The separated collagen is salt-treated for fractionation and ethanol-treated for obtaining 5~10% of collagen from the initial tissue weight. The prepared tissues are processed for separating collagen through the collagen separating process. The separated collagen is processed for preparing product. The method for preparing product is comprised: treating a collagen solution having a predetermined concentration under a neutral condition at a low temperature, followed by overnight treatment at a temperature of 30 to 35° C.; concentrating collagen by centrifugation; and dissolving the thus-concentrated collagen in refrigerated weakly-acidic solvent or phosphate buffered saline (PBS), thereby preparing collagen having a concentration of 1 to 5 mg/mL.

16 Claims, 2 Drawing Sheets

Fig.1

1. Collagen standard  2. Marker  3. Collagen (from tendon)  4. Collagen (from bone)
5. Collagen (from skin)

METHOD OF SEPARATING COLLAGEN FROM THE VARIOUS ANIMAL TISSUES FOR PRODUCING COLLAGEN SOLUTION AND PRODUCT USING THE SAME

TECHNICAL FIELD

The present invention relates to a method for separation of collagen from various animal tissues, a method for preparing a collagen solution and a product manufactured using the same. More specifically, the present invention relates to a method for efficient separation of collagen from animal bone and cartilage tissues, skin tissues and tendon/ligament tissues, a method for preparing a collagen solution from such isolated tissues, and a collagen matrix and highly-concentrated collagen solution using the same.

BACKGROUND ART

As is generally known, collagen is a protein of the scleroprotein class which constitutes bones, cartilage, teeth, tendons and skin of animals and also scales of fish. Collagen is present as a fiber-like solid and exhibits the intricate cross-striated periodic structure upon examining under an electron microscope.

Collagen is a structural protein that is most frequently found in all kinds of mammals, and comprises about 30% of the total weight of all proteins in the body. At present, 20 species of collagen are known and type I collagen is the most abundant form of collagen. Collagen has a structure in which monomer proteins having a molecular weight of about 300 kDa are cross-linked with each other via covalent bonding at specific sites. Therefore, matured collagen forms a characteristic fiber-like shape having water-insolubility and high tensile strength. Collagen is composed of constituting amino acids such as glycine, proline, hydroxyproline, alanine and glutamic acid, and is particularly characterized by a high content of hydroxyproline that is not usually found in other forms of proteins.

Meanwhile, such collagen has a structure in which three polypeptide strands are twisted in spiral fashion around one another, via hydrogen bonds. Collagen is not decomposed in water, dilute acids and dilute alkalis, but boiling of collagen results in conversion thereof into a single-stranded structure of gelatin that is soluble. Unlike gelatin, collagen can acquire suitable viscosity without warming and therefore can be conveniently prepared when it is subjected to gelation. In addition, due to its higher molecular weight than gelatin, collagen is more biocompatible with biotissues and exhibits high physiological activity. Therefore, when it is used to treat wounds, collagen facilitates a healing process, which is in contrast to the tendency in which gelatin interferes with tissue regeneration. In addition, collagen is highly flexible even when it is hardened, and rapidly cross-links within a short period of time, thus resulting in a reduced gelling time. Collagen is not susceptible to action of proteolytic enzymes such as trypsin, pepsin, ficin, papain and elastinase, whereas it is susceptible to decomposition by collagenase. Separation of collagen from tissues involves organic solvent extraction, acid/alkali treatment, followed by action of proteolytic enzymes such as trypsin, pepsin, ficin, papain and elastinase, thereby obtaining collagen.

In addition, for in vivo applications, the thus-obtained collagen is dissolved in biologically non-toxic solvents, for example buffers such as water, physiological saline and borate buffer, or aqueous solutions containing salts, for example sodium chloride, proteins, saccharides and fats.

Many studies are currently underway for the development of an efficient method for separating collagen. In order to secure sufficient quantities of collagen for medical use, large amounts of raw materials are necessary and significant advancement is also required in an separation method of collagen.

In particular, it is known that collagen not only plays a role in an increase of a concentration of blood platelets and aggregation of blood platelets but also serves to activate blood platelets via deformation of shapes or biochemical structures of blood platelets, and therefore collagen is widely used as a hemostatic.

Numerous methods for separating collagen have been known since the 1950s, but there is a difficulty in separation of pure collagen in a non-denaturated form. Therefore, there still remains a requirement for the development of a method that is capable of separating collagen from a variety of tissues and in large amounts, in order to use collagen in various fields.

However, currently known methods of separating collagen primarily lie in separation of collagen from skin or tendons of mammals (murine, bovine, porcine and the like). Unfortunately, there is as yet no method capable of separating collagen from bone tissues.

DISCLOSURE OF INVENTION

Technical Problem

Therefore, the present invention has been made in view of the above problems, and it is a first object of the present invention to provide a method for separation and utilization of collagen from various tissues of animals.

For this purpose, a second object of the present invention is to provide a method for efficient separation of collagen from bone and cartilage tissues, skin tissues and tendon/sinew tissues of animals.

A third object of the present invention is to provide a method for preparing a collagen solution from such separated tissues.

A fourth object of the present invention is to provide a collagen matrix and highly-concentrated collagen solution using the above collagen solution.

A fifth object of the present invention is to provide a method for separating collagen from various tissues of animals, a method for preparing a collagen solution and a product manufactured using the same, which are suited for enhancing customer satisfaction via remarkably improved quality and reliability of the product.

Technical Solution

In accordance with an aspect of the present invention, the above and other objects can be accomplished by the provision of a method for preparing a collagen solution from various tissues of an animal, comprising, upon final treatment of collagen, treating a collagen solution having a predetermined concentration under neutral conditions at a low temperature, followed by overnight treatment at a temperature of 30 to 35° C.; concentrating collagen by centrifugation; and dissolving the thus-concentrated collagen in refrigerated weakly-acidic solvent or phosphate buffered saline (PBS), thereby preparing a solution having a collagen concentration of 1 to 5 mg/mL.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

The preferred embodiments of the present invention for accomplishing the above-mentioned objects will now be described in more detail with reference to the accompanying drawings.

A method for separating collagen from various tissues of animals, a method for preparing a collagen solution and a product manufactured using the same, which are applied to the present invention, are constituted as shown in FIGS. 1 through 4.

In connection with description of the present invention hereinafter, if it is considered that description of known functions or constructions related to the present invention may make the subject matter of the present invention unclear, the detailed description thereof will be omitted.

Terms which will be described hereinafter are established taking into consideration functions in the present invention and may vary according to manufacturer's intention or a usual practice in the related art. Therefore, the terms used herein should be defined based on the contents of the specification of the present invention.

The present invention is directed to an improved method for efficiently separating collagen from a variety of tissues, particularly a method for separating collagen from bone tissues, and an application method of the separated collagen.

As used herein, the term "separated collagen" refers to that from which peptides having strong antigenicity were removed by treating collagen, extracted from various animals, with acids or enzymes such as pepsin, trypsin, chymotrypsin, papain and ficin.

Collagen in accordance with the present invention exhibits solubility at a temperature of 4 to 10° C. under acidic pH conditions, but insolubility at a temperature of 30 to 37° C. under neutral pH conditions. In addition, when collagen at a pre-determined concentration is stood at a temperature of 30 to 37° C. with respect to changes of acidity from an acidic pH value to a neutral pH value, collagen in accordance with the present invention exhibits a gel form. Application of a certain stimulus to collagen results in a change from the gel form to the insoluble fiber-like form.

In a method to which proper temperature and pH are applied, titration of collagen at a neutral pH while maintaining the temperature condition of 4° C. can retain properties of the solution phase for a predetermined period of time even under neutral conditions.

Additionally, separation of collagen is intended to be carried out taking advantage of differences in changes of pH and temperatures, differences in differential salt concentrations and ethanol precipitation.

Further, the present invention will be used as a method for concentrating collagen by standing a collagen solution at a temperature of 30 to 37° C. under neutral conditions for a predetermined period of time to induce layer separation, and precipitating collagen by centrifugation.

As discussed hereinbefore, collagen increases a concentration of blood platelets and causes aggregation of blood platelets, and also deforms shapes or biochemical structures of blood platelets, thereby activating blood platelets. Therefore collagen is also widely used as a hemostatic.

It is known that the viscosity of collagen relative to pH is highest in a pH range of 5.0 to 6.0.

For this, upon final treatment of collagen in accordance with the present invention, a collagen solution having a predetermined concentration is treated at a low temperature under neutral conditions and is then treated at a temperature of 30 to 35° C. overnight while applying a predetermined shaking. After overnight treatment, collagen is concentrated by centrifugation and the thus-concentrated collagen is dissolved in weakly-acidic solvent or phosphate buffered saline (PBS), which was kept in cold storage, thereby preparing a collagen solution having a concentration of 1 to 5 mg (collagen)/mL.

Collagen in accordance with the present invention can be applied in the form of a matrix or a highly-concentrated solution.

Figure 3:
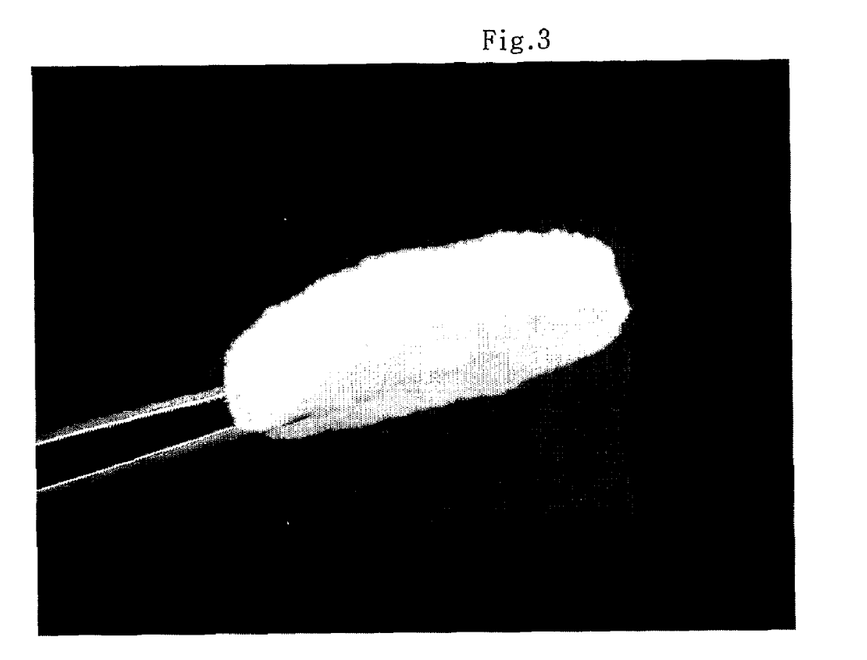
FIG. 3 is a photograph of a matrix product manufactured using collagen in accordance with the present invention.

That is, as shown in FIG. 3, the matrix is prepared by injecting filtered pure air into collagen at a suitable concentration and pH to thereby form predetermined pores, followed by lyophilization and dry-heat drying.

Here, the collagen matrix is made of a collagen solution having a collagen concentration of 3 to 5 mg/mL. Specifically, filtered pure air is injected into the collagen solution at a pH of 5.0 to 6.0, thereby forming predetermined pores. The pore-formed collagen solution is then lyophilized, packaged by heat treatment and sterilized with ethylene oxide (EO) gas or gamma-ray (γ-ray) irradiation, thereby forming a collagen matrix. The matrix may be constructed in various forms depending upon types of molds used. The thus-constructed matrix may be used as a hemostatic, a support and the like, and various forms of the collagen hemostatic and supports are currently commercially available on the market. Further, the collagen matrix may include other components such as fibrinogen and thrombin to enhance effects of collagen as the hemostatic. Such a collagen matrix may also be used as hemostatic adhesive bandages.

Figure 4:
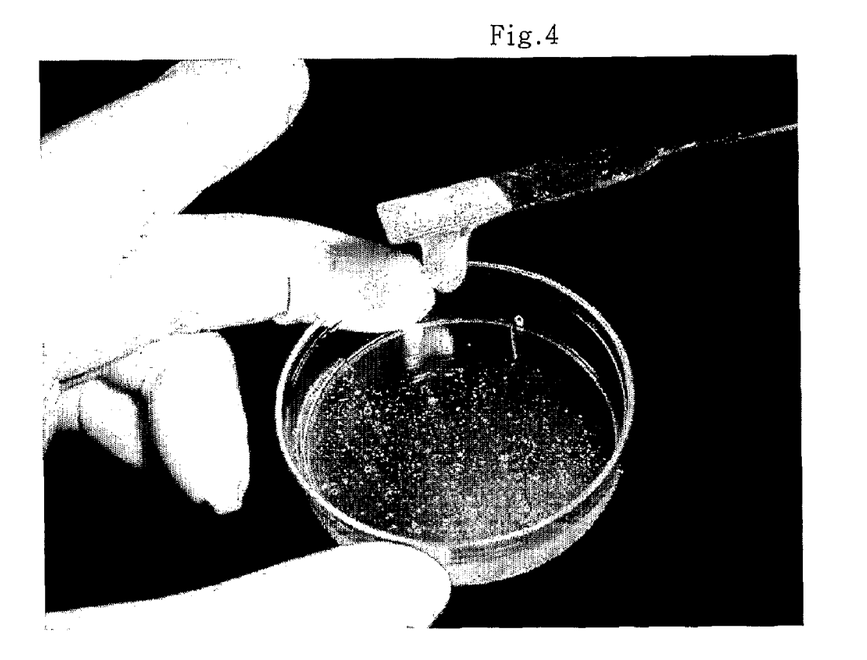
FIG. 4 is a photograph of a highly-concentrated collagen solution product manufactured using collagen in accordance with the present invention.

In order to utilize a highly-concentrated collagen solution as shown in FIG. 4, the present invention prepares a collagen solution by sterilizing collagen at a concentration of 1 mg/mL through a 0.22 μm filter and concentrating the sterilized collagen to obtain a 3 to 7% collagen solution. The highly-concentrated collagen solution is used as filler for removing wrinkles on the skin, and is also commercially available as the corresponding product. In addition, using the highly-concentrated collagen solution containing antibiotic substances or growth factors, it is possible to induce issue regeneration effects in wounds and damaged regions by spraying the collagen solution thereon.

MODE FOR THE INVENTION

Examples

Now, the present invention will be described in more detail with reference to the following examples. These examples are provided only for illustrating the present invention and should not be construed as limiting the scope and spirit of the present invention.

Example 1

Porcine bone tissue was made into a powder having a particle size of 1 to 500 μm and was acid-treated with 0.5N HCl. Then, the acid-treated bone tissue was repeatedly treated with pepsin (2 to 5 times) for a long period of time (3 to 7 days) to separate type I collagen which was then subjected to salt treatment for fractionation and ethanol treatment, thereby obtaining collagen as 5 to 10% of the initial tissue weight. Specifically, this procedure will be described in more detail hereinafter:

1. Porcine-isolated bone tissue was thoroughly washed with distilled water, ethanol, acetone and the like.
2. The bone tissue was cut into a doughnut shape and stored at −20° C.
3. In order to separate collagen from the bone tissue, the bone tissue was made into a powder having a particle size of 1 to 500 μm.
4. The pulverized bone tissue was washed with ethanol and distilled water.
5. The thus-washed bone powder was treated overnight with 0.5N HCl while being shaken at 10 to 100 rpm.
6. After overnight treatment, the bone powder was treated with pepsin (pepsin was treated in a 10 to 50:1 ratio of the tissue:pepsin, and was dissolved in 0.1N HCl prior to use).
7. Pepsin treatment was repeated 2 to 5 times for 3 to 7 days.
8. The pepsin-treated bone powder solution was centrifuged at 4° C. and 12,000 g for 30 min, and a supernant was separated and stored and a precipitate was returned to Step 7.
9. A final concentration of 0.5 to 0.8M NaCl was applied to the separated and stored supernant which was then treated at 4° C. for 4 hours to 1 day.
10. After centrifugation (12,000 g, 30 min and 4° C.), a precipitate was removed and a supernant was collected.
11. The supernant was titrated under neutral conditions and a final concentration of the solution was made to 1.6M NaCl.
12. The resulting solution was treated at 4° C. for 4 hours to 1 day and centrifuged, and a precipitate was removed again and a supernant was collected.
13. NaCl was additionally added to the collected supernant to a final concentration of 2.6M NaCl, followed by standing at 4° C. for 4 hours to 1 day.
14. Centrifugation was carried out to remove a supernant, and the resulting precipitate was washed once or twice with 95% ethanol and resuspended in distilled water.
15. 1N HCl was added to the resuspended solution in an amount of 1 mL:100 mL ratio to accomplish complete resuspension and titrated again at 4° C. under neutral conditions.
16. The thus-titrated solution was stood at a temperature of 30 to 37° C. for 4 hours to 1 day and then centrifuged, and
17. The thus-precipitated collagen was resuspended to a concentration of 1 to 30 mg/mL in weakly acidic solvent or PBS, and stored at 4° C.

Example 2

Porcine cartilage tissue was made into a powder and was acid-treated with 0.5N HCl. Then, the acid-treated cartilage tissue was repeatedly treated with pepsin to separate type II collagen which was then subjected to salt treatment for fractionation and ethanol treatment, thereby obtaining collagen as 5 to 10% of the initial tissue weight. Specifically, this procedure will be described in more detail hereinafter:

1. Porcine-isolated cartilage tissue was thoroughly washed with distilled water, ethanol, acetone and the like.
2. In order to separate collagen from the cartilage tissue, the cartilage tissue was made into a powder having a particle size of 1 to 500 μm.
3. The pulverized cartilage tissue was washed with ethanol and distilled water.
4. The thus-washed cartilage tissue was treated overnight with a guanidine-HCl solution (4M guanidine-HCl, 0.05M Tris-HCl, pH 7.5),
5. The overnight-treated cartilage powder was washed once or twice with 0.1N HCl.
6. The cartilage powder was treated overnight with 0.5N HCl while being shaken at 10 to 100 rpm.
7. After overnight treatment, the cartilage powder was treated with pepsin (pepsin was treated in a 10 to 50:1 ratio of the tissue:pepsin, and was dissolved in 0.1N HCl prior to use).
8. Pepsin treatment was repeated 2 to 5 times for 3 to 7 days.
9. The pepsin-treated cartilage powder solution was centrifuged at 4° C. and 12,000 g for 30 min, and a supernant was separated and stored and a precipitate was returned to Step 8.
10. A final concentration of 0.5 to 0.8M NaCl was applied to the separated and stored supernant which was then treated at 4° C. for 4 hours to 1 day.
11. After centrifugation (12,000 g, 30 min and 4° C.), a precipitate was removed and a supernant was collected.
12. The supernant was titrated under neutral conditions and a final concentration of the solution was made to 2.6M NaCl.
13. The resulting solution was treated at 4° C. for 4 hours to 1 day and centrifuged, and a precipitate was removed again and a supernant was collected.
14. NaCl was additionally added to the collected supernant to a final concentration of 3.5 to 4.0M NaCl, followed by standing at 4° C. for 4 hours to 1 day.
15. Centrifugation was carried out to remove a supernant, and the resulting precipitate was washed once or twice with 95% ethanol and resuspended in distilled water.
16. 1N HCl was added to the resuspended solution in an amount of 1 mL:100 mL ratio to accomplish complete resuspension and titrated again at 4° C. under neutral conditions.
17. The thus-titrated solution was stood at a temperature of 30 to 37° C. for 4 hours to 1 day and then centrifuged, and
18. The thus-precipitated collagen was resuspended to a concentration of 1 to 30 mg/mL in weakly acidic solvent or PBS, and stored at 4° C.

Example 3

Porcine skin tissue was made into a section (500 μm to 5 μm thickness), and the tissue section was placed in a net having a lattice size of 200 to 500 μm and (was acid-treated with 0.1N HCl. Then, the acid-treated tissue) was repeatedly treated with pepsin to separate type I collagen which was then subjected to salt treatment for fractionation and ethanol treatment, thereby obtaining collagen as 10 to 15% of the initial tissue weight. Specifically, this procedure will be described in more detail hereinafter:

1. Porcine-isolated skin tissue was thoroughly washed with distilled water, ethanol and the like, and stored at −20° C.
2. In order to separate collagen from the skin tissue, the skin tissue was made into a section having a thickness of 500 μm to 5 mm.
3. The tissue section was placed in a net having a lattice size of 200 to 500 μm and washed with ethanol and distilled water.
4. The thus-washed tissue section was treated with pepsin (pepsin was treated in a 10 to 50:1 ratio of the tissue:pepsin, and was dissolved in 0.1N HCl prior to use).

5. Pepsin treatment was repeated 2 to 3 times for 2 to 3 days.

6. The pepsin-treated skin tissue solution was centrifuged at 4° C. and 12,000 g for 30 min, and a supernant was separated and stored and a precipitate was returned to Step 5.

7. A final concentration of 0.5 to 0.8M NaCl was applied to the separated and stored supernant which was then treated at 4° C. for 4 hours to 1 day.

8. After centrifugation (12,000 g, 30 min and 4° C.), a precipitate was removed and a supernant was collected.

9. The supernant was titrated under neutral conditions and a final concentration of the solution was made to 1.6M NaCl.

10. The resulting solution was treated at 4° C. for 4 hours to 1 day and centrifuged, and a precipitate was removed again and a supernant was collected.

11. NaCl was additionally added to the collected supernant to a final concentration of 2.6M NaCl, followed by standing at 4° C. for 4 hours to 1 day.

12. Centrifugation was carried out to remove a supernant, and the resulting precipitate was washed once or twice with 95% ethanol and resuspended in distilled water.

13. 1N HCl was added to the resuspended solution in an amount of 1 mL:100 mL ratio to accomplish complete resuspension and titrated again at 4° C. under neutral conditions.

14. The thus-titrated solution was stood at a temperature of 30 to 37° C. for 4 hours to 1 day and then centrifuged, and 15. The thus-precipitated collagen was resuspended to a concentration of 1 to 30 mg/mL in weakly acidic solvent or PBS, and stored at 4° C.

Example 4

Porcine tendon/ligament tissue was made into a section (500 μm to 5 mm thickness) and was treated with pepsin to separate type I collagen which was then subjected to salt treatment for fractionation and ethanol treatment, thereby separating collagen as 10 to 20% of the initial tissue weight. Specifically, this procedure will be described in more detail hereinafter:

1. Porcine-isolated tendon/ligament tissue was thoroughly washed with distilled water, ethanol and the like, and stored at −20° C.

2. In order to separate collagen from the tendon/ligament tissue, the tendon/ligament tissue was made into a section having a thickness of 500 μm to 5 mm.

3. The tissue section was washed with ethanol and distilled water.

4. The thus-washed tissue section was treated with pepsin (a 10 to 50:1 ratio of the tissue:pepsin, dissolved in 0.1N HCl prior to use).

5. Pepsin treatment was repeated 2 to 3 times for 2 to 3 days.

6. The pepsin-treated tendon/ligament tissue solution was centrifuged at 4° C. and 12,000 g for 30 min, and a supernant was separated and stored and a precipitate was returned to Step 5.

7. A final concentration of 0.5 to 0.8M NaCl was applied to the separated and stored supernant which was then treated at 4° C. for 4 hours to 1 day.

8. After centrifugation (12,000 g, 30 min and 4° C.), a precipitate was removed and a supernant was collected.

9. The supernant was titrated under neutral conditions and a final concentration of the solution was made to 1.6M NaCl.

10. The resulting solution was treated at 4° C. for 4 hours to 1 day and centrifuged, and a precipitate was removed again and a supernant was collected.

11. NaCl was additionally added to the collected supernant to a final concentration of 2.6M NaCl, followed by standing at 4° C. for 4 hours to 1 day.

12. Centrifugation was carried out to remove a supernant, and the resulting precipitate was washed once or twice with 95% ethanol and resuspended in distilled water.

13. 1N HCl was added to the resuspended solution in an amount of 1 mL:100 mL ratio to accomplish complete resuspension and titrated again at 4° C. under neutral conditions.

14. The thus-titrated solution was stood at a temperature of 30 to 37° C. for 4 hours to 1 day and then centrifuged, and 15. The thus-precipitated collagen was resuspended to a concentration of 1 to 30 mg/mL in weakly acidic solvent or PBS, and stored at 4° C.

Figure 1:
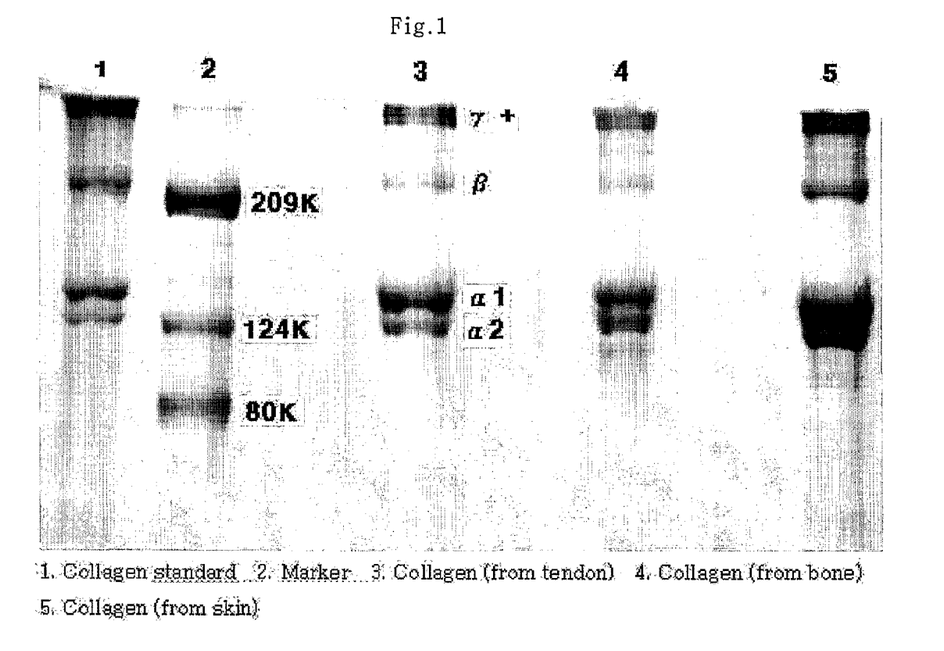
FIG. 1 is a photograph showing patterns and results of SDS-PAGE of collagen applied to the present invention, based on size separation of protein.

By effects of the above-mentioned Examples 1 through 4, it could be confirmed from the results of SDS-PAGE analysis shown in FIG. 1 that molecular weights of the corresponding bands were about 140 kDa and 130 kDa, respectively.

Figure 2:
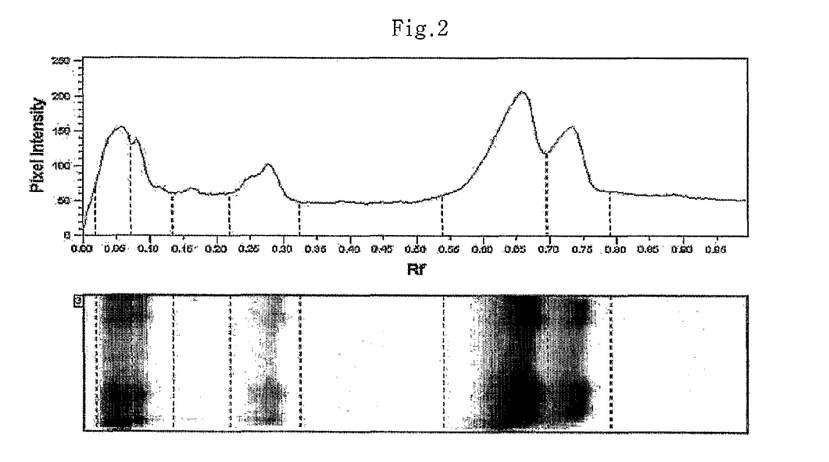
FIG. 2 is a graph and photograph showing analysis results of collagen applied to the present invention, using an image analyzer.

In addition, from the results of image analysis of collagen shown in FIG. 2, it could be confirmed that the characteristic of type I collagen, i.e. a ratio of α1:α2 is 2:1 (a value of test results). FIG. 3 shows a photograph of a matrix product manufactured using collagen in accordance with the present invention, and FIG. 4 shows a photograph of a highly-concentrated collagen solution product manufactured using collagen in accordance with the present invention.

INDUSTRIAL APPLICABILITY

As apparent from the above description, the present invention enables separation and utilization of collagen from various tissues of animals. For this purpose, specific objects of the present invention are to provide a method for efficient separation of collagen from bone, cartilage, skin and tendon/ligament tissues of animals, preparation of a collagen solution from such isolated tissues, and preparation of a matrix and highly-concentrated solution using the collagen solution. Therefore, the present invention accomplishes remarkably improved quality and reliability of the product and thereby is very useful to enhance customer satisfaction.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for separating collagen from an animal tissue, the method comprising steps of:
    a. washing an animal tissue thoroughly with distilled water, ethanol and acetone, wherein said animal tissue is a porcine-isolated bone tissue;
    b. cutting the washed bone tissue from step (a) into a doughnut shape and storing the cut bone tissue at −20° C.;
    c. processing the stored bone tissue from step (b), comprising pulverizing the stored bone tissue into a powder having a particle size from 1 μm to 500 μm;
    d. washing the pulverized bone tissue powder from step (c) with ethanol and distilled water;
    e. acid-treating the washed bone powder from step (d) comprising contacting the washed bone powder with 0.5N HCl, and agitating 10 to 100 rpm, thereby providing an acid-treated bone tissue powder;
    f. pepsin-treating the acid-treated bone tissue powder from step (e), comprising;
        i dissolving an amount of pepsin in 0.1N HCl; and then ii adding the pepsin to the acid-treated bone tissue powder in a ratio of tissue:pepsin from 10:1 to 50:1; and
iii repeating step (f)(ii) 2 to 5 times and for a period of 3 to 7 days, thereby providing a pepsin-treated bone powder solution containing a type I collagen separated from the pepsin-treated bone powder;
g. obtaining a supernatant and a precipitate from the pepsin-treated bone powder solution, comprising:
i. centrifuging the pepsin-treated bone powder solution at 4° C. and 12,000 g for 30 minutes; then
ii. separating the supernatant from the centrifuged solution and storing the separated supernatant; and
iii. pepsin-treating the precipitate 2 to 5 times and for a period of 3 to 7 days;
h. adjusting the separated, stored supernatant from step (g) to a NaCl concentration of 0.5M to 0.8M NaCl;
i. maintaining the NaCl-adjusted supernatant from step (h) at 4° C. and for a period of time from 4 hours to 1 day;
j. centrifuging the maintained supernatant from step (i) at 4° C. and 12,000g for 30 minutes, and then removing a precipitate and collecting a supernatant formed therefrom;
k. titrating the supernatant from step (j) with NaCl at a neutral pH, comprising adding NaCl to the supernatant of step (j) thereby obtaining a solution having a concentration to 1.6M NaCl;
l. maintaining the supernatant-containing solution of step (k) at 4° C. and for a period of time from 4 hours to 1 day, followed by centrifuging the supernatant-containing solution, and then removing a precipitate and collecting a supernatant formed therefrom;
m. adding NaCl to the collected supernatant from step (l) thereby obtaining a 2.6M NaCl concentrate, and maintaining the 2.6M NaCl concentrate at 4° C. and for a period of 4 hours to 1 day;
n. centrifuging the 2.6M NaCl concentrate obtained form step (m) and then removing a supernatant from a precipitate thus formed;
o. washing the precipitate from step (n) once or twice with 95% ethanol, and then resuspending the ethanol-washed precipitate in distilled water, thereby forming a resuspended solution;
p. adding volume of 1N HCl to the volume of the resuspended solution of step (o) in ratio of 1:100(v/v), thereby providing a completely resuspended solution and then titrating the completely resuspended solution at a temperature of 4° C. and at a neutral pH;
q. maintaining the titrated solution from step (p) at 30° C. to 37° C. and for a period of time from 4 hours to 1 day;
r. centrifuging the maintained solution from step (q) and obtaining a collagen-containing precipitate therefrom;
s. resuspending the collagen-containing precipitate from step (r) to a concentration of 1 to 30 mg/mL by resuspending said collagen-containing precipitate in a weakly acidic solvent or phosphate-buffered saline (PBS) and then maintaining the resuspended collagen-containing concentrate at 4° C.;
t. salt-treating the collagen-containing concentrate from step (s); and then
u. obtaining the separated collagen from the salt-treated, collagen-containing concentrate of step (t), wherein said separated collagen comprises the type I collagen and comprises from 5 to 10% of the weight of the bone tissue from step (a).

2. The method of separating collagen of claim 1, wherein the obtaining of the separated collagen of step (u) comprises:

i. storing the collagen-containing concentrate at 30° C. to 35° C. for a period of 1 day;
ii. centrifuging the stored collagen-containing concentrate of step (u)(i), thereby further concentrating the collagen contained therein; and
iii. dissolving the further-concentrated collagen from step (u)(ii) in a refrigerated weakly-acidic solvent or PBS, thereby preparing the collagen solution having a concentration of 1 mg/mL to 5 mg/mL.

3. The method of separating collagen of claim 2, wherein the obtaining of the separated collagen of step (u) further comprises:
iv. adjusting the collagen solution from step (u)(iii) to a concentration of 3 mg/mL to 5 mg/mL and pH of 5.0 to 6.0 and then injecting therein a filtered, purified air to form a collagen solution having plurality of pores; and
v. lyophilizing the pore-formed collagen solution from step (u)(iv) and then treating the lyophilized collagen with heat and with sterilizing ethylene oxide (EO) gas or gamma-ray (γ-ray) irradiation.

4. The method of separating collagen of claim 2, the method further comprising:
iv. adjusting the concentration of the collagen solution of step (u)(iii) to 1 mg/mL and then sterilizing by filtering the thus adjusted solution through a filter having a 0.22 μm pore size, thereby providing a sterilized collagen solution; and
v. concentrating the sterilized collagen solution from step (u)(iv) to prepare a 3% to 7% concentrated collagen solution.

5. A method for separating collagen from an animal tissue, the method comprising steps of:
a. washing an animal tissue thoroughly with distilled water, ethanol, and acetone, wherein said animal tissue is a porcine-isolated cartilage tissue;
b. processing the washed cartilage tissue comprising pulverizing the washed cartilage tissue into a powder having a particle size from 1 μm to 500 μm;
c. washing the pulverized cartilage tissue powder from step (b) with ethanol and distilled water;
d. treating the washed cartilage tissue powder from step (c) with a solution consisting of 4M guanidine-HCl and 0.05M Tris-HCl the solution having a pH of 7.5;
e. washing the treated cartilage powder from step (d) once or twice with 0.1N HCl,
f. acid-treating the washed cartilage powder from step (e), comprising contacting the washed cartilage powder with 0.5N HCl and agitating at 10 to 100 rpm, thereby providing an acid-treated cartilage powder;
g. pepsin-treating the acid-treated cartilage powder from step (f), comprising:
i. dissolving an amount of pepsin in 0.1 N HCL; and then
ii. adding the pepsin to the acid-treated cartilage powder in a ratio of cartilage powder:pepsin from 10:1 to 50:1; and
iii. repeating step (g)(ii) 2 to 5 times and for a period of 3 to 7 days, thereby providing a pepsin-treated cartilage powder solution containing a type II collagen separated from the pepsin-treated cartilage powder;
h. obtaining a supernatant and a precipitate from the pepsin-treated cartilage powder solution, comprising:
i. centrifuging the pepsin-treated cartilage powder solution at 4° C. and 12,000 g for 30 minutes; then
ii. separating the supernatant from the centrifuged solution and storing the separated supernatant; and
iii. pepsin-treating the precipitate 2 to 5 times and for a period of 3 to 7 days;

i. adjusting the separated, stored supernatant from step (h)(ii) to a NaCl concentration of 0.5M to 0.8M NaCl;
j. maintaining the NaCl-adjusted supernatant from step (i) at 4° C. and for a period of time from 4 hours to 1 day;
k. centrifuging the maintained supernatant from step (j) at 4° C. and 12,000 g for 30minutes, and then removing a precipitate and collecting a supernatant formed therefrom;
l. titrating the supernatant from step (k) with NaCl at a neutral pH, comprising adding NaCl to the supernatant of step (k), thereby obtaining a solution having a concentration to 1.6M NaCl;
m. maintaining the supernatant-containing solution of step (l) at 4° C. and for a period of time from 4 hours to 1 day, followed by centrifuging the supernatant-containing solution, and then removing a precipitate and collecting a supernatant formed therefonn;
n. adding NaCl to the collected supernatant from step (m) thereby obtaining a 2.6M NaCl concentrate, and maintaining the 2.6M NaCl concentrate at 4° C. and a period of 4 hours to 1 day;
o. centrifuging the 2.6M NaCl concentrate obtained form step (n) and then removing a supernatant from a precipitate thus formed;
p. washing the precipitate from step (o) once or twice with 95% ethanol, and then resuspending the ethanol-washed precipitate in distilled water, thereby forming a resuspended solution;
q. adding volume of 1N HCl to the volume of the resuspended solution of step (p)in ratio of 1:100(v/v), thereby providing a completely resuspended solution and then titrating the completely resuspended solution at a temperature of 4° C. and at a neutral pH;
r. maintaining the titrated solution from step (q) at 30° C. to 37° C. and for a period of time from 4 hours to 1 day;
s. centrifuging the maintained solution from step (r) and obtaining a collagen-containing precipitate therefrom;
t. resuspending the collagen-containing precipitate from step (s) to a concentration of 1 to 30 mg/mL by resuspending said collagen-containing precipitate in a weakly acidic solvent or phosphate-buffered saline (PBS) and then maintaining the resuspended collagen-containing concentrate at 4° C.;
u. salt-treating the collagen-containing concentrate from step (t); and then v. obtaining the separated collagen from the salt-treated, collagen-containing concentrate of step (u), wherein said separated collagen comprises the type II collagen and comprises from 5 to 10% of the weight of the cartilage tissue from step (a).

6. The method of separating collagen of claim 5, wherein the obtaining of the separated collagen of step (v) further comprises:
i. storing the collagen-containing concentrate at 30° C. to 35° C. for a period of 1 day;
ii. centrifuging the stored collagen-containing concentrate of step (v)(i), thereby further concentrating the collagen contained therein; and
iii. dissolving the further-concentrated collagen from step (v)(ii) in a refrigerated weakly-acidic solvent or PBS, thereby preparing the collagen solution having a concentration of 1 mg/mL to 5 mg/mL.

7. The method of separating collagen of claim 6, wherein the obtaining of the separated collagen of step (v) further comprises:
iv. adjusting the collagen solution from step (v)(iii) to a concentration of 3 mg/mL to 5 mg/mL and pH of 5.0 to 6.0 and then injecting therein a filtered, purified air to form a collagen solution having plurality of pores; and
v. lyophilizing the pore-formed collagen solution from step (u)(iv) and then treating the lyophilized collagen with heat and with sterilizing ethylene oxide (EO) gas or gamma-ray (γ-ray) irradiation.

8. The method of separating collagen of claim 6, wherein the obtaining of the separated collagen of step (v) further comprises:
iv. adjusting the concentration of the collagen solution of step (v)(iii) to 1 mg/mL and then sterilizing by filtering the thus adjusted solution through a filter having a 0.22 μm pore size, thereby providing a sterilized collagen solution; and
v. concentrating the sterilized collagen solution from step (v)(iv) to prepare a 3% to 7% concentrated collagen solution.

9. A method of separating collagen from an animal tissue, the method comprising the steps of:
a. washing an animal tissue thoroughly with distilled water and ethanol and then storing the washed tissue at −20° C., wherein said animal tissue is a porcine-isolate skin tissue;
b. processing the washed, stored skin tissue from step (a), comprising sectioning the washed, stored skin tissue to a thickness of 500 μm to 5 mm;
c. washing the sectioned skin tissue from step (b), comprising placing the sectioned skin tissue from step (b) into a net said net having a lattice size of 200 μm to 500 μm and then washing with ethanol and distilled water;
d. pepsin-treating the washed, sectioned skin tissue from step (c), comprising:
i. dissolving an amount of pepsin in 0.1N HCl; and then
ii. adding the pepsin to the washed, sectioned skin tissue in a ratio of washed, sectioned skin tissue:pepsin from 10:1 to 50:1; and
iii. repeating step (d)(ii) 2 to 3 times and for a period of 2 to 3 days, thereby providing a pepsin-treated skin solution containing a type I collagen separated from the pepsin-treated skin;
e. obtaining a supernatant and a precipitate from the pepsin-treated skin solution, comprising:
i. centrifuging the pepsin-treated skin solution at 4° C. and 12,000 g for 30 minutes; then
ii. separating the supernatant from the centrifuged solution and storing the separated supernatant; and
iii. pepsin-treating the precipitate 2 to 3 times and for a period of 2 to 3 days;
f. adjusting the separated, stored supernatant from step (e)(ii) to a NaCl concentration of 0.5M to 0.8M NaCl;
g. maintaining the NaCl-adjusted supernatant from step (f) at 4° C. and for a period of time from 4 hours to 1 day;
h. centrifuging the maintained supernatant from step (g) at 4° C. and 12,000 g for 30 minutes, and then removing a precipitate and collecting a supernatant formed therefrom;
titrating the supernatant from step (h) with NaCl at a neutral pH, comprising adding NaCl to the supernatant of step (h) thereby obtaining a solution having a concentration to 1.6M NaCl;
j. maintaining the supernatant-containing solution of step (i) at 4° C. and for a period of time from 4 hours to 1 day, followed by centrifuging the supernatant-containing solution, and then removing a precipitate and collecting a supernatant formed therefrom;

k. adding NaCl to the collected supernatant from step (j) thereby obtaining a 2.6M NaCl concentrate, and maintaining the 2.6M NaCl concentrate at 4° C. and for a period of 4 hours to 1 day;

l centrifuging the 2.6M NaCl concentrate obtained form step (k) and then removing a supernatant from a precipitate thus formed;

m. washing the precipitate from step (l) once or twice with 95% ethanol, and then resuspending the ethanol-washed precipitate in distilled water, thereby forming a resuspended solution;

n. adding volume of 1N HCl to the volume of the resuspended solution of step (m) in ratio of 1:100(v/v), thereby providing a completely resuspended solution and then titrating the completely resuspended solution at a temperature of 4° C. and at a neutral pH;

o. maintaining the titrated solution from step (n) at 30° C. to 37° C. and for a period of time from 4 hours to 1 day;

p. centrifuging the maintained solution from step (o) and obtaining a collagen-containing precipitate therefrom;

q. resuspending the collagen-containing precipitate from step (p) to a concentration of 1 to 30 mg/mL by resuspending said collagen-containing precipitate in a weakly acidic solvent or phosphate-buffered saline (PBS) and then maintaining the resuspended collagen-containing concentrate at 4° C.;

r. salt-treating the collagen-containing concentrate from step (q); and then s. obtaining the separated collagen from the salt-treated, collagen-containing concentrate of step (r), wherein said separated collagen comprises the type I collagen and comprises from 10 to 15% of the weight of the skin tissue from step (a).

10. The method of separating collagen of claim 9, wherein the obtaining of the separated collagen of step (s) further comprises:

i. storing the collagen-containing concentrate at 30° C. to 35° C. for a period of 1 day;

ii. centrifuging the stored collagen-containing concentrate of step (s)(i), thereby further concentrating the collagen contained therein; and iii. dissolving the further-concentrated collagen from step (s)(ii) in a refrigerated weakly-acidic solvent or PBS, thereby preparing the collagen solution having a concentration of 1 mg/mL to 5 mg/mL.

11. The method of separating collagen of claim 10 wherein the obtaining of the separated collagen of step (s) further comprises:

iv. adjusting the collagen solution from step (s)(iii) to a concentration of 3 mg/mL to 5 mg/mL and pH of 5.0 to 6.0 and then injecting therein a filtered, purified air to form a collagen solution having plurality of pores; and v. lyophilizing the pore-formed collagen solution from step (u)(iv) and then treating the lyophilized collagen with heat and with sterilizing ethylene oxide (EO) gas or gamma-ray (γ-ray) irradiation.

12. The method of separating collagen of claim 10, wherein the obtaining of the separated collagen of step(s) further comprises:

iv. adjusting the concentration of the collagen solution of step(v)(iii) to 1 mg/mL and then sterilizing by filtering the thus adjusted solution through a filter having a 0.22 μm pore size, thereby providing a sterilized collagen solution; and v. concentrating the sterilized collagen solution from step (v)(iv) to prepare a 3% to 7% concentrated collagen solution.

13. A method for separating collagen from an animal tissue, the method comprising steps of:

a. washing an animal tissue thoroughly with distilled water and ethanol, and then storing the washed tissue at −20° C., wherein said animal tissue is a porcine-isolated tendon or ligament tissue;

b. processing the washed, stored tendon or ligament tissue from step (a), comprising sectioning the washed, stored tendon or ligament tissue to a thickness of 500 μm to 5 mm;

c. washing the sectioned tissue of step (b) with ethanol and distilled water;

d. pepsin-treating the washed, sectioned tendon or ligament tissue from step (c), comprising:
  i. dissolving an amount of pepsin in 0.1N HCl; and then
  ii. adding the pepsin to the acid-treated tendon or ligament in a ratio of tendon:pepsin or ligament:pepsin from 10:1 to 50:1; and
  iii. repeating step (d)(ii) 2 to 3 times and for a period of 2 to 3 days, thereby providing a pepsin-treated tendon or ligament solution containing a type I collagen separated from the pepsin-treated tendon or ligament;

e. obtaining a supernatant and a precipitate from the pepsin-treated tendon or ligament solution, comprising:
  i. centrifuging the pepsin-treated tendon or ligament solution at 4° C. and 12,000 g for 30 minutes; then
  ii. separating the supernatant from the centrifuged solution and storing the separated supernatant; and
  iii. pepsin-treating the precipitate 2 to 3 times and for a period of 2 to 3 days;

f. adjusting the separated, stored supernatant from step (e)(ii) to a NaCl concentration of 0.5M to 0.8M NaCl;

g. maintaining the NaCl-adjusted supernatant from step (f) at 4° C. and for a period of time from 4 hours to 1 day;

h. centrifuging the maintained supernatant from step (g) at 4° C. and 12,000 g for 30 minutes, and then removing a precipitate and collecting a supernatant formed therefrom;

i. titrating the supernatant from step (h) with NaCl at a neutral pH, comprising adding NaCl to the supernatant of step (h) thereby obtaining a solution having a concentration to 1.6M NaCl;

j. maintaining the supernatant-containing solution of step (i) at 4° C. and for a period of time from 4 hours to 1 day, followed by centrifuging the supernatant-containing solution, and then removing a precipitate and collecting a supernatant formed therefrom;

k. adding NaCl to the collected supernatant from step (j) thereby obtaining a 2.6M NaCl concentrate, and maintaining the 2.6M NaCl concentrate at 4° C. and for a period of 4 hours to 1 day;

l. centrifuging the 2.6M NaCl concentrate obtained form step (k) and then removing a supernatant from a precipitate thus formed;

m. washing the precipitate from step (l) once or twice with 95% ethanol, and then resuspending the ethanol-washed precipitate in distilled water, thereby forming a resuspended solution;

n. adding volume of 1N HCl to the volume of the resuspended solution of step (m) in ratio of 1:100(v/v), thereby providing a completely resuspended solution and then titrating the completely resuspended solution at a temperature of 4° C. and at a neutral pH;

o. maintaining the titrated solution from step (n) at 30° C. to 37° C. and for a period of time from 4 hours to 1 day;

p. centrifuging the maintained solution from step (o) and obtaining a collagen-containing precipitate therefrom;

q. resuspending the collagen-containing precipitate from step (p) to a concentration of 1 to 30-mg/mL by resuspending said collagen-containing precipitate in a weakly acidic solvent or phosphate-buffered saline (PBS) and then maintaining the resuspended collagen-containing concentrate at 4° C.;

r. salt-treating the collagen-containing concentrate from step (q); and then s. obtaining the separated collagen from the salt-treated, collagen-containing concentrate of step (r), wherein said separated collagen comprises the type I collagen and comprises from 10 to 20% of the weight of the tendon or ligament tissue from step (a).

14. The method of separating collagen of claim 13, wherein the obtaining of the separated collagen of step (s) comprises:
   i. storing the collagen-containing concentrate at 30° C. to 35° C. for a period of 1day;
   ii. centrifuging the stored collagen-containing concentrate of step (s)(i), thereby further concentrating the collagen contained therein; and
   iii. dissolving the further-concentrated collagen from step (s)(ii) in a refrigerated weakly-acidic solvent or PBS, thereby preparing the collagen solution having a concentration of 1 mg/mL to 5 mg/mL.

15. The method of separating collagen of claim 14, wherein the obtaining of the separated collagen of step (s) further comprises:
   iv. adjusting the collagen solution from step (s)(iii) to a concentration of 3 mg/mL to 5 mg/mL and pH of 5.0 to 6.0 and then injecting therein a filtered, purified air to form a collagen solution having plurality of pores; and
   v. lyophilizing the pore-formed collagen solution from step (u)(iv) and then treating the lyophilized collagen with heat and with sterilizing ethylene oxide (EO) gas or gamma-ray ($\gamma$-ray) irradiation.

16. The method of separating collagen of claim 14, wherein the obtaining of the separated collagen of step (s) further comprises:
   iv. adjusting the concentration of the collagen solution of step (v)(iii) to 1 mg/mL and then sterilizing by filtering the thus adjusted solution through a filter having a 0.22 µm pore size, thereby providing a sterilized collagen solution; and
   v. concentrating the sterilized collagen solution from step (v)(iv) to prepare a 3% to 7% concentrated collagen solution.

* * * * *